United States Patent [19]

Braatz et al.

[11] Patent Number: 4,940,737
[45] Date of Patent: Jul. 10, 1990

[54] CHEMICALLY MODIFIED HYDROPHILIC PREPOLYMERS AND POLYMERS

[75] Inventors: James A. Braatz, Beltsville; Aaron H. Heifetz, Columbia, both of Md.; Richard A. Wolfe, Ellisville, Mo.; Narender P. Luthra, Columbia, Md.

[73] Assignee: W. R. Grace & Co.-Conn, New York, N.Y.

[21] Appl. No.: 266,445

[22] Filed: Nov. 2, 1988

[51] Int. Cl.$^5$ ............................................. C08G 18/14
[52] U.S. Cl. ................................ 521/103; 521/129; 521/159; 521/905; 524/839; 524/591; 524/498; 528/53; 528/57; 528/59; 528/904
[58] Field of Search ............... 521/905, 159, 129, 103; 524/916, 839, 591, 498; 528/53, 904, 49, 57, 59; 527/202

[56] References Cited

U.S. PATENT DOCUMENTS

| | | | |
|---|---|---|---|
| 3,723,393 | 3/1973 | Kistner | 528/61 |
| 3,939,123 | 2/1976 | Matthews et al. | |
| 4,137,200 | 1/1979 | Wood et al. | |
| 4,177,038 | 12/1979 | Biebricher et al. | |
| 4,182,827 | 1/1980 | Jones | |
| 4,226,935 | 10/1980 | Fusee | |
| 4,293,679 | 10/1981 | Cogliano | 528/48 |
| 4,439,585 | 3/1984 | Gould et al. | |
| 4,485,227 | 11/1984 | Fox | |
| 4,499,233 | 2/1985 | Tetenbaum et al. | 524/591 |
| 4,569,981 | 2/1986 | Wenzel et al. | |
| 4,681,851 | 7/1987 | Baumgarten et al. | |

OTHER PUBLICATIONS

Smith et al., "Urethans of 2-Mercaptoethanol", J. Amer. Chem. Soc., vol. 81 (1959) pp. 161-163.
Ulrich et al., "Base-Catalyzed Reactions of Isocyanates. The Synthesis of 2,4-Dialkylallophanates", J. Org. Chem., vol. 32, (1967) pp. 3938-3941.
Farkas et al., "Catalytic Effects in Isocyanate Reactions", Advan. Catalysis, vol. 13 (1962) pp. 434-439.

Primary Examiner—Maurice J. Welsh
Attorney, Agent, or Firm—W. R. Grace & Co.-Conn.

[57] ABSTRACT

A class of modified hydrophilic prepolymers and polymers is disclosed which are characterized by their specific reactivity. Isocyanate-capped oxyethylene-based prepolymers are modified by reacting with a compound having an isocyanate-reactive group which is a sulfhydryl group, an amino group, a hydroxyl group or a carboxyl group, and a non-isocyanate-reactive group, in quantities sufficient to modify at least a portion of the isocyanate groups of the prepolymer. Where said first functional group is an amino group contained in a diamine or polyamine compound or is a carboxyl group, the modifying compound is present in quantities sufficient to modify all or substantially all of the isocyanate groups of the prepolymer.

32 Claims, No Drawings

CHEMICALLY MODIFIED HYDROPHILIC PREPOLYMERS AND POLYMERS

BACKGROUND OF THE INVENTION

This invention relates to a unique series of modified or derivatized prepolymers and polymers formed from isocyanate end-capped prepolymers which are substantially comprised of ethylene oxide units. Modification is accomplished by contacting the prepolymer with a reactive compound having an NCO-reactive group and a second functional group. The NCO-reactivity can be found in sulfhydryl (—SH), amine (—NH$_2$), alcohol (—OH) or carboxyl (—COOH) groups. The derivative compounds are characterized by additional properties associated with the second functional group inserted into the prepolymer. Hydrogels, coatings or small soluble polymeric or prepolymeric units can be formed from the modified prepolymers.

Numerous polyurethane polymers have been previously identified, among them both foamed and non-foamed materials. Of the nonfoamed materials, quite a few hydrogel polymers, prepared from various prepolymers, have been prepared and used for widely varying applications. Typically, hydrogels are formed by polymerizing a hydrophilic monomer in an aqueous solution under conditions such that the prepolymer becomes crosslinked, forming a three-dimensional polymeric network which gels the solution. Polyurethane hydrogels are formed by polymerization of isocyanate-end capped prepolymers to create urea and urethane linkages.

Representative examples of previously disclosed polyurethane hydrogels include the following: U.S. Pat. No. 4,241,537 (Wood) discloses a plant growth media comprising a hydrophilic polyurethane gel composition prepared from chain-extended polyols; random copolymerization is preferred with up to 50% propylene oxide units so that the prepolymer will be a liquid at room temperature. U.S. Pat. No. 3,939,123 (Matthews) discloses lightly crosslinked polyurethane polymers of isocyanate terminated prepolymers comprised of poly(ethyleneoxy) glycols with up to 35% of a poly(propyleneoxy) glycol or a poly(butyleneoxy) glycol. In producing the Matthews polymer, an organic polyamine is used as a crosslinking agent. The Matthews prepolymers form a cross-linked, three dimensional structure when polymerized as taught in the patent. U.S. Pat. No. 4,182,827 (Jones) discloses a similar use of polyamines in the formation of polyurethane hydrogels.

Several types of compounds have been reacted with prepolymers or with matrix bases to act as spacing or coupling compounds in the attachment or immobilization of biologically active agents. For example, U.S. Pat. No. 4,226,935 (Fusee) discloses reacting an amino acid and/or a protein with an excess of a urethane prepolymer, curing the resulting product to form a polymer matrix, and coupling an enzyme thereto by use of a carbodiimide. U.S. Pat. No. 4,177,038 (Biebricher et al.) teaches the use of spacers which may be diamines, amino-alcohols or diols.

Modified polyurethane polymers also have been prepared. U.S. Pat. No. 4,439,585 (Gould et al.) teaches a polyurethane diacrylate composition obtained by reacting a diacrylate in the presence of a hydrophilic polyurethane resin. U.S. Pat. No. 4,485,227 (Fox) discloses a poly-(ether-urethane-urea) prepared by condensations of a prepolymer with primary diamines, then with an amine-reacting agent. U.S. Pat. No. 4,569,981 (Wenzel et al.) discloses water-dispersible plastics precursors based on isocyanate-terminated prepolymers which have been hydrophilically modified with ionic groups and/or ethylene oxide groups.

Biocompatibility is an increasingly desirable characteristic for polymeric hydrogels and hydrated polymers, which would find numerous uses in the health care field if the appropriate properties can be obtained. However, many conventional hydrogels and polymers are not taught to be biocompatible.

SUMMARY OF THE INVENTION

The polyurethane polymer system of this invention provides modified prepolymers and polymers having highly desirable properties which make them particularly well suited for use in the growing field of biological and biomedical applications. The modified prepolymers and polymers of this invention are prepared by modifying or derivatizing isocyanate end-capped prepolymers in aqueous or organic solution. Particularly suitable are prepolymers substantially or exclusively comprised of ethylene oxide units.

The modified hydrated polymers may take the form of water-swellable three-dimensional hydrogels or foams. Alternatively, they may take the form of a dense or thin coating or impregnant on a substrate, including, under dilute conditions, a monomolecular or substantially monomolecular layer. The coatings and impregnates of this invention are considered gels or hydrogels and are included by those terms unless otherwise noted. The terms gel or hydrogel are meant to refer to polymers which are non-foamed in structure. In still another embodiment, higher proportions of the isocyanates are modified, yielding individual modified prepolymer molecules which are water soluble and which are largely incapable of forming a polymeric structure, although some polymerization may occur.

It is a particular purpose of this invention to provide modified prepolymers and polymers with altered properties. The modified compounds of this invention may be hydrophilic and biocompatible. At the same time, they are specifically reactive or adsorptive to particular compounds or classes of compounds, depending on the second functional group inserted into the prepolymer by the modification or derivatization reaction. It is intended that the modified polymers or prepolymers of this invention exhibit one or more of the following properties or capabilities: enhancement of cell growth in mammalian cell culture, enhancement of antibody production by hybridoma cells, alteration of in vivo circulating half-life of therapeutic agents, formation of reversible hydrogels, reduction of corrosion of metals in aqueous solutions, or other activity or reactivity. The added properties are not considered limited by this list, but will vary depending on the modifying compound.

It is an additional object of this invention to provide a class of modified hydrated prepolymers and polymers for which ease of preparation and handling is combined with desirable properties permitting a wide range of end uses. In this regard, the modified prepolymers disclosed herein can be handled and stored in liquid form at ambient temperatures. This significantly facilitates formation of the hydrated polymer, as well as enhances the uniformity of the polymer.

DETAILED DESCRIPTION OF THE INVENTION

A new class of modified hydrophilic polyurea-urethane prepolymers and related modified polymers has been found which are uniquely characterized by specific reactivity due to the addition of a specific functional group to the prepolymer molecule. The prepolymers from which the modified compounds are prepared are polymeric monomer units which are oxyethylene-based alcohols which include monofunctional alcohols, diols and polyols with essentially all of the hydroxyl groups capped with polyisocyanate. The prepolymer is modified or derivatized by reaction with a compound having a first functional group which is NCO-reactive. The terms "modified" and "derivatized" will be used interchangeably herein. The modifying compound also has a second functional group which is non-reactive with the NCO groups of the prepolymer or is less reactive, preferably substantially less reactive, with the NCOs than the NCO-reactive group (that is, than the first functional group). The NCO-reactive group may be a sulfhydryl (—SH), amino (—NH$_2$), hydroxyl (—OH) or carboxyl (—COOH) group.

Polymerization of partially modified prepolymers in water or an aqueous solution acts to gel the solution or a deposited layer of the composition, or to cause formation of a foam, depending on the prepolymer. Where small modified polymeric units or completely modified prepolymer units are formed, the modified compound will be soluble in water but will not actually form a gel or foam by polymerization through the NCO groups. It is possible, however, that polymerization could occur by virtue of the second functional group of the modifying compound, or other functional groups of that compound.

Prepolymer Preparation

The prepolymers utilized in this invention are prepared from oxyalkylene-based alcohols. These can be monofunctional alcohols or they can be diols or polyols, including diols or polyols made up of ethylene oxide monomer units. The proportion of ethylene oxide units may vary, and is described in more detail below. Prepolymers are formed when diols and/or polyols are end-capped with di- or polyfunctional isocyanates as described below. In certain embodiments (i.e., where polymerization is not required), monofunctional alcohols may be end-capped with di- or polyfunctional isocyanates for use in this invention. These compounds are not, strictly speaking, "prepolymers." However, since they are prepared and used in an analogous manner, the term "prepolymer" as used herein will refer to isocyanate-capped monofunctional alcohols as well as diols or polyols.

One extensive class of hydrophilic, isocyanate-capped urethane prepolymer is described in U.S. Pat. No. 4,137,200 (Wood et al.), the teachings of which are incorporated herein. The Wood et al. prepolymers are blends of a monomeric polyol and polyoxyalkylene glycol, the hydroxyl groups of the blend being capped with a polyisocyanate. The polyoxethylene polyol may have a weight average molecular weight of about 100 to about 20,000, and preferably between about 600 to about 6000, with a hydroxyl functionality of about 2 or greater, preferably from about 2 to about 8. The polyols should desirably have about 40 to about 100 mole percent ethylene oxide content.

It is possible, and may be desirable, to incorporate various amounts of a relatively hydrophobic comonomer. Thus, comonomers such as propylene oxide or butylene oxide may be copolymerized as a random copolymer, block-copolymer, or both. Aliphatic, aromatic or aliphatic-aromatic isocyanates may be used, such as those listed hereinbelow. Optionally, a cross-linking agent may be included.

One group of isocyanate-capped urethane prepolymers of this class that can be used in the invention comprises the isocyanate-capped polyesters. Such prepolymers may be made by condensing a polyhydric alcohol with a polycarboxylic acid to form a linear polyester which is then reacted with a slight molar excess of a polyisocyanate to provide an essentially linear polyurethane having terminal isocyanate groups and having an average molecular weight within the range 100 to 20,000, preferably between about 600 to about 6000. Polyhydric alcohols that can be used in preparing such prepolymers include the polyalkylene glycols such as ethylene, propylene and butylene glycol and polymethylene glycols such as tetramethylene and hexamethylene glycols. Another group of isocyanate capped urethane prepolymers that can be used in the invention comprise the isocyanate capped polyethers. These prepolymers can be made by reacting, for example, polyalkylene glycols with diisocyanates of the type listed below to provide a polyurethane having terminal isocyanate groups and having an average molecular weight within the range 100 to 20,000, preferably between about 600 to about 6000. As specific examples of these prepolymers, the HYPOL ™ polyurethane prepolymer series available from Grace Specialty Chemicals Co., W. R. Grace & Co.-Conn., is suitable A second class of prepolymers suitable for use in this invention comprises polyoxyalkylene diols or polyols which are of generally higher molecular weights and which are predominantly or exclusively made up of ethylene oxide monomer units. This second class is somewhat more preferred for use in this invention. Preferably, at least 75% of the monomer units should be ethylene oxide, more preferably at least 90%, and most preferably at least 95% up to about 100%. As specific examples of this class of prepolymers, prepolymers from the BIOPOL ™ polyurethane prepolymer series available from Grace Specialty Chemicals Co., W. R. Grace & Co.-Conn., will be particularly suitable. These prepolymers will form hydrogels when partially modified as described below.

High molecular weight ethylene oxide-based diols and polyols are used to prepare this second class of prepolymers, derivatized prepolymers and hydrated polymers of the present invention. The diol or polyol molecular weight prior to capping with polyisocyanate preferably should be at least about 7000 to 8000 MW, more preferably about 10,000 to about 30,000 MW. It is preferred to use trihydroxy compounds (triols) in the preparation of the polyols which are the precursors to the prepolymers, derivatized prepolymers and hydrated polymers of this invention. For example, glycerol is a preferred triol. Trimethylolpropane (TMOP), trimethylolethane and triethanolamine are other suitable triols. In addition, tetrols, such as pentaerythritol, may be used to prepare polyols for use in this invention. Triol- or tetrol-based polyols are capped with difunctional or polyfunctional isocyanate compounds as described below to form the prepolymer.

Alternatively, diols of appropriate molecular weight may be used as precursors to the prepolymers of this invention. Diols of appropriate molecular weight are capped with polyfunctional isocyanates as described below to form the prepolymers. High molecular weight polyethylene glycols are particularly useful. Especially desirable in this embodiment are polyethylene glycols of the formula $H(OCH_2CH_2)_xOH$ where x is an average number such that the glycol has an average molecular weight of at least about 7000, preferably about 10,000 to about 30,000. Alternatively, diols may be capped with diisocyanates and used in conjunction with crosslinking compounds to form the hydrated polymers described herein. Crosslinking compounds useful for this purpose include polyfunctional amines and polyfunctional isocyanates. In still another alternative embodiment, diols may be mixed with polyols and the resulting mixture reacted with isocyanates to produce the prepolymer of this invention.

Monofunctional alcohols may be selected as the basic "prepolymer" unit where completely modified prepolymer units are intended. For example, mono-methoxy poly(ethylene glycol) can be used. In this embodiment, the monofunctional alcohol is end-capped with polyisocyanate and then modified according to this invention. These modified compounds will not be capable of polymerization. Rather, they will result in small, completely modified prepolymer units which are soluble in water.

The prepolymers of this second class are formed by reacting the hydroxyl groups of the diols or polyols described above with polyisocyanates. "Polyisocyanate" as used herein is intended to refer to both diisocyanates and polyisocyanates, as appropriate, except as indicated by specifying the use of difunctional or polyfunctional isocyanates. Isocyanate end-capped (i.e., isocyanate-terminated) prepolymers are formed.

The selected precursor to the prepolymer influences the choice of polyisocyanate in that the prepolymer structure must lend itself to sufficient crosslinking to gel an aqueous prepolymer solution or to form a crosslinked polymeric coating where those properties are desired. In the embodiment in which the precursors to the prepolymers are polyols (that is, triol-based or tetrol-based), difunctional isocyanates are preferred. If desired, polyfunctional isocyanate compounds may also be used with polyols. Mixtures of suitable isocyanates also may be considered.

Where diols are used as the precursors to the prepolymers, they may be reacted with polyfunctional isocyanate compounds to form the prepolymers of this invention. This combination yields prepolymers having sufficient functional groups for crosslinking in the formation of the hydrated polymer. In an alternative embodiment using diols as the precursors to the prepolymers, the diols may be capped with a difunctional isocyanate. In order to achieve sufficient crosslinking in the hydrated polymer prepared from these difunctional prepolymers, they are used in conjunction with a crosslinking compound. The preferred crosslinker is trimethylolpropane ("TMOP"), although others may be used, for example, glycerol, trimethylolethane, pentaerythritol, triethanolamine, polyfunctional amines, polyfunctional isocyanates, and the like.

Aromatic, aliphatic or cycloaliphatic polyisocyanates may be used in any of the above-described embodiments. The use of aliphatic polyisocyanates permits a greater degree of handling and/or shaping since aliphatic isocyanate-capped prepolymers typically require about 20 to 90 minutes to gel to a hydrated polymer state. By contrast, prepolymers capped with aromatic polyisocyanates will gel more rapidly, in about 30 to 60 seconds. In addition, aliphatic polyisocyanates will be preferred when the hydrated polymer is intended to be used in medical applications, because of decreased toxicological considerations. However, hydrated polymers made using aromatic polyisocyanates in the prepolymer are also useful, as well as being suitable for most industrial uses.

Examples of suitable di- and polyfunctional isocyanates are found in the following list:
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
4,4'-diphenylmethane diisocyanate
3,3'-dichloro-4,4'-biphenylene diisocyanate
1,6-hexamethylene diisocyanate
1,4-tetramethylene diisocyanate
1,10-decamethylene diisocyanate
cumene-2,4-diisocyanate
1,5-napthalene diisocyanate
methylene dicyclohexyl diisocyanate
1,4-cyclohexylene diisocyanate
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyante
2,4-dimethyl-1,3-phenylene diisocyante
5,6-dimethyl-1,3-phenylene diisocyanate
2,4-diisocyanatodiphenylether
4,4'-diisocyanatodiphenylether
benzidine diisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenylmethane
2,6-dimethyl-4,4'-diisocyanatodiphenyl
2,4-diisocyanatostilbene
3,3'-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate
p,p',p''-triphenylmethane triisocyanate
trifunctional trimer (isocyanurate) of isophorone diisocyanate
trifunctional biuret of hexamethylene diisocyanate
trifunctional trimer (isocyanurate) of hexamethylene diisocyanate
polymeric 4,4'-diphenylmethane diisocyanate Capping of the selected diols or polyols with polyisocyanates to form the prepolymers of this invention is effected using stoichiometric amounts of reactants. The isocyanate-to-hydroxyl group ratio preferably should be between about 1.8 and about 2.2. Higher ratios may be used but are not preferred since they may lead to problems associated with excessive monomer present in the final products. The capping reaction may be by any convenient method or procedure. For example, the reaction may be carried out at about 20 to about 150° C, under dry nitrogen, for about 2 hours to about 14 days, preferably in the absence of a catalyst. The preferred temperature is about 60 to 70° C. The reaction is terminated when the isocyanate concentration approaches theoretical values. The time period will be a function of the polyisocyanate used and the temperature at which the reaction is conducted.

It is preferred to avoid using an excess of polyisocyanate in preparing the prepolymer. Preferably, an isocyanate-to-hydroxyl group ratio of 2:1 (for example, one diisocyanate molecule per hydroxyl group of the polyol) is used to ensure complete end-capping of the polyol. Complete end-capping eliminates excessively high viscosity in the prepolymer by avoiding undue amounts of chain extension. However, a slight excess of isocyante, i.e., up to about ten percent, can be used.

It is characteristic of this second polymer system that the isocyanate content of the prepolymer is very low. This is achieved by employing high molecular weight polyols and by avoiding excessive quantities of isocyanate in the end-capping reaction so that free isocyanate monomers are unlikely to be present. The isocyanate concentration in the prepolymer should be about 0.1 to about 0.43 milliequivalents per gram, for prepolymers formed from diols or polyols of about 7,000 to 30,000 MW.

Notwithstanding a preference for low isocyanate content, the polymer system described herein affords a greater degree of flexibility in this regard than conventional systems. The presence of the organic solvent in preparing and handling the prepolymer protects against excessive viscosity resulting from the use of polyols of higher molecular weight or increased EO content, or from the use of insufficient quantities of isocyanate for complete end-capping of the diol or polyol. That is, the organic solvent permits the use of less than stoichiometric (2:1) quantities of the isocyanate monomer. Chain extension resulting from incomplete end-capping typically results in increased viscosity which may make handling of the prepolymer difficult or impossible. By contrast, the system of this invention tends not to be affected negatively by increased viscosity due to chain extension, or from any other cause, because the solvent serves to maintain the viscosity within a range suitable for convenient handling of the prepolymer.

The organic solvent used in preparing the prepolymer must be compatible with the reactants and with the end use desired for the hydrated polymer. Primarily, the solvent must be one in which the diol or polyol and/or prepolymer can be readily dissolved, preferably at ambient temperatures. Suitable solvents for preparing the prepolymer include acetonitrile, dimethyl formamide, dimethyl sulfoxide, tetrahydrofuran, dioxane, dichloromethane, acetone and methyl ethyl ketone, or mixtures thereof. Acetonitrile is preferred.

In one embodiment using an organic solvent, the diol or polyol itself is dissolved in the solvent and is reacted with polyisocyanate while in solution to yield the isocyanate end-capped prepolymer. This embodiment is particularly preferred where the diol or polyol is solid or crystalline at ambient temperatures, that is, for diols or polyols substantially or exclusively comprised of ethylene oxide units and for high molecular weight diols or polyols. In this manner, even crystalline diols or polyols can easily be handled without heating to their respective melting points. Even though the prepolymer formation reaction is conducted at elevated temperatures, utilizing an organic solvent to first place the diol or polyol in liquid form assures good reaction and prepolymer formation.

In another embodiment using an organic solvent, the isocyanate end-capped prepolymer first is prepared and then is dissolved in an organic solvent. This embodiment will be useful where the diol or polyol already is liquid or pasty at ambient temperatures and does not require dissolution in order to prepare the prepolymer. For example, diols or polyols of lower molecular weight or higher propylene oxide or butylene oxide content may be treated in this manner. Use of a solvent at the prepolymer stage is advantageous where increased viscosity occurs due to chain extension of incompletely end-capped diols or polyols.

It may be desired to add an antioxidation agent, preferably prior to preparation of the prepolymer. Antioxidants are not required to make or use the prepolymers or polymers of this invention. However, storage and handling properties may be enhanced by such an addition by preventing oxidative breakdown of the polymer or its precursors. Suitable antioxidants include the hindered phenolic compounds. Specific examples are Irganox TM (Ciba-Geigy Corp.) and Santonox TM (Monsanto Chemical Co.). The antioxidant may be added in amounts of about 0.01 to about 1.0%, preferably about 0.02 to about 0.1%, based on the weight of the polyol or precursor to the prepolymer.

Modifyinq Compounds

Prepolymers prepared as described above are modified or derivatized to add specific reactivity to the basic polymeric compound which is to be prepared. Specific functionality and reactivity can be imparted to an otherwise nonreactive, biocompatible polymer in this manner. As an example, in embodiments in which a polymerized structure is formed, the surface of the polymer may be generally nonadsorptive and nonreactive with the exception of the desired functionality inserted into the polymer by the process described here.

The prepolymer is modified by reacting it with a compound containing a first functional group which is isocyanate-reactive and a second functional group which imparts the desired specific reactivity to the modified prepolymer. The second functional group is isocyanate-non-reactive or is substantially less reactive with isocyanates than the first functional group. The isocyanate-reactive functional group is a sulfhydryl (—SH), amino (—NH$_2$), hydroxyl (—OH) or carboxyl (—COOH) group. The rate and extent of the modification reaction will depend in part on the first functional group of the modifying compound (that is, the NCO-reactive group) and in part on the relative molar quantities of the prepolymer and the modifying compound. Where the first functional group is an amino group contained in a diamine or polyamine compound or is a carboxyl group, a large molar excess of the modifying compound is used so that substantially all of the isocyanate groups of the prepolymer are modified.

In general, sulfhydryl groups react preferentially and rapidly with the isocyanate ("NCO') groups of the prepolymers, under conditions which cause formation of the thiolate ion (—S$^-$), as described below. The thiolate ion reacts with the isocyanate groups of the prepolymer to provide modified prepolymers containing —NH-C(O)S-(thiourethane) linkages, even in the presence of amino, hydroxyl or carboxyl functional groups.

However, isocyanate-capped prepolymers will react substantially faster with sulfhydryl-containing compound than with the compounds containing the other listed groups only when reacted under conditions in which the thiolate anion (—S⁻) is formed as the active species. Conversely, under conditions where a sulfhydryl-containing compound will not readily form the thiolate reactive group, the prepolymer modification reaction will proceed very slowly and may not occur to any appreciable extent. That is, the presence of the sulfhydryl group alone is not sufficient for the modification reaction in the absence of suitable conditions to form the thiolate ion. For example, reaction of prepolymer and ethanethiol ($C_2H_5SH$) in acetonitrile solvent will not proceed in the absence of a catalyst to ionize the sulfhydryl group of ethanethiol.

The thiolate anion may be formed catalytically by the addition of an extramolecular catalyst. Suitable catalysts would include base catalysts (preferably a tertiary amine such as triethylamine or N-methyl imidazole) or reducing agents such as sodium borohydride. In certain cases, intramolecular or self-catalysis may occur to cause formation of the thiolate ion.

One example of a compound undergoing intramolecular catalysis is cysteamine, formed by treating cystamine (($NH_2CH_2CH_2)_2S_2$) with a reducing agent. Specifically, in the presence of mercaptoethanol or another reducing agent, the disulfide bond of cystamine is reduced to form cysteamine ($NH_2CH_2CH_2SH$) which contains both a free amino and a free sulfhydryl group. The amino and sulfhydryl groups of the cysteamine molecule interact to cause formation of the thiolate ion by intramolecular catalysis. The NCO groups of the prepolymer react preferentially with the thiolate group of the self-catalyzed cysteamine molecule, yielding a prepolymer modified via the thiolate so as to have a free amino group as the second functional group.

Alternatively, cystamine itself can be reacted with the prepolymer prior to reduction of the disulfide bond. In this case, the NCO groups of the prepolymer will react with the free amino groups of the cystamine molecule, the second functional group being blocked by the disulfide bond. Following cystamine modification of the prepolymer, a reducing agent such as mercaptoethanol is added to reduce the disulfide bond, creating the sulfhydryl group, which is the second functional group in this embodiment.

By contrast, reaction of NCO-capped prepolymers with compounds containing an amino group as the first functional group is relatively slower than reaction with thiolate-containing compounds, although reaction is still quite rapid. The amino-NCO reaction forms modified prepolymers containing —NHC(0)NH—(urea) linkages. Reaction rates between the prepolymer and modifying compounds containing amino groups will vary with pH. Unprotonated amines are preferred for faster reaction rates.

Where diamines or polyamines are used as the modifying compound, they should be employed in large excess quantities in order to cause modification of the prepolymer. By "large excess quantities" is meant greater than a 1:1 molar ratio of —$NH_2$ to —NCO groups, preferably greater than 2:1 and most preferably between about 2:1 and about 5:1. It should be understood that use of small amounts of primary or secondary diamines or polyamines will serve the function of crosslinking the modified prepolymer by reacting with the NCO-groups of multiple prepolymer molecules. This is taught in prior patents such as Matthews et al., described above. However, when used in large excess quantities, the diamines and polyamines do not serve the crosslinking function, since it is unlikely that any polyamine molecule will react with NCO-groups from more than one prepolymer molecule. Rather, the reaction serves to derivatize the prepolymer in the manner of this invention. Monoamines may be reacted in any desired relative quantity.

Reaction of NCO-capped prepolymers with compounds containing hydroxyl groups is slower still, forming modified prepolymers containing —NHC(O)O— (urethane) linkages. Under conditions where the hydroxyl group is maintained, reaction is quite slow. Examples include methanol, ethanol, ethylene glycol, etc. Methanol will react with the prepolymer to form a modified prepolymer having a methyl group as the second functional group. However, reaction may be very fast where the —$O^{31}$ (alkoxide) ion is formed. For example, methoxide or ethyl alkoxide would be suitable modifying compounds and would be reactive.

The fourth category of first functional groups useful in forming the modified prepolymers and polymers of this invention includes compounds having carboxyl (—COOH) groups. Compounds with aliphatic or aromatic carboxyl groups may be used. For example, certain amino-protected amino acids and peptides might be reacted with the prepolymer via the carboxyl group. As another example, 2,2-dithiodiethanoic acid can be used as the modifying compound. However, reaction of the prepolymer NCO groups with a carboxylic acid is very slow. The reaction rate can be accelerated by the addition of a base (e.g., triethylamine, N-methyl imidazole, etc.) to ionize the carboxyl group. The modified prepolymers will contain anhydride or amide linkages.

As with diamine- or polyamine-modifying compounds, compounds containing carboxyl groups should be employed in large excess quantities in order to modify the prepolymer. By "large excess quantities" is meant greater than a 1:1 molar ratio of —COOH to —NCO groups, preferably greater than 2:1 and most preferably between about 2:1 and about 5:1. When used in these large excess quantities, complete or substantially complete modification of the prepolymer —NCO groups occurs.

Examples of suitable modifying compounds with which the prepolymer may be reacted according to this invention include the following:
2-aminoethanol (ethanolamine)
aminoethyl hydrogensulfate
aminoethane sulfonic acid (taurine)
4-aminosulfonyl-1-hydroxy-2-naphthoic acid
glucosamine
5-(aminosulfonyl) N-((1-ethyl-2-pyrrolidinyl) methyl)-2-methoxybenzamide
sulfamylphenyl-D-glucosylamine
4-carboxybenzene-sulfonamide
sulfanilamide
cyclic-AMP
2-aminoethyl phosphonic acid
tyrosine
tyramine
dibutylamine L- or DL-cysteine (alpha-amino-beta-thiol propionic acid)
L- or DL-cysteine ethyl ester
L- or DL-cystine dimethyl ester
L- or DL-cystine (di(alpha-amino-beta-thiol propionic acid)
L- or DL-cysteinesulfonic acid
L- or DL-cysteic acid
cystamine (2,2-dithiobis(ethylamine))
2-mercaptoethanol
ethanethiol
glutathione
3-amino-1,2-propanediol
3-amino-1-propane sulfonic acid
3-aminophenyl boronic acid
2-amino-2-deoxy-D-galactose (galactosamine)
1-amino-1-deoxy-D-galactose
p-aminophenyl-alpha-D-glucose
p-aminophenyl-1-thio-beta-D-galactose
penicillamine.

In addition to these specific examples, compounds from the following groups may be used:
peptides with sulfhydryl groups
peptides with free amino groups
animal hormones
polysaccharides
lipids
nucleic acids
amino sugars
amino acids
amine surfactants
diamine and polyamines It may be desired to temporarily block the second functional group of the modifying compound in order to ensure that modification of the prepolymer takes place via the first functional group. This will allow for preparation of the desired modified prepolymer, without contamination from competing modification reactions. For example, where a modifying compound contains both amino and carboxyl groups, it may be desired to block the amino groups to allow modification via the carboxyl groups. Blocking procedures for various functional groups are well known. Following prepolymer modification, the second functional group is de-blocked, again by well-known procedures.

Prepolymer Modification Reaction

The reaction between the prepolymer and the modifying compound may be conducted in a variety of ways by manipulating the order of addition as well as the environment in which the reaction is conducted (i.e., aqueous or nonaqueous). In addition, the degree of prepolymer modification may be controlled by the relative molar quantities of the components.

In one order of addition, the reaction may be commensed by adding the modifying compound to the prepolymer. Preferably, the modifying compound is used in a nonaqueous solution. This will result in relatively low levels of prepolymer modification, although the extent of modification also will be affected by the molar concentrations. It is preferred to use this order of addition where only small degrees of modification are desired. It is, for example, most preferred where the modifying compound is a diamine or polyamine or contains a carboxyl group. Moreover, this order specifically is not preferred where the modifying compound is a diamine or polyamine since crosslinking would be the predominant reaction, as described in Matthews et al., above. Rather, where diamines or polyamines are used, it is preferred to use them primarily or exclusively as modifying compounds. Similarly, this order of addition is not preferred for use with carboxyl group-containing modifying compounds, since only low levels of modification will be achieved. Extensive to complete modification is ensured by using the second, preferred, order of addition described below, and also by using large molar excesses of the modifying compound where that compound is a diamine, polyamine or contains carboxyl groups.

In the second, preferred, order of addition, the prepolymer is added to a nonaqueous solution of the modifying compound. Preferably, a large molar excess of the modifying compound is used where extensive or complete modification is desired. This order of addition is particularly preferred for use with diamines, polyamines and compounds containing carboxyl groups as the first functional group so that the modification reaction occurs prior to any significant amount of polymerization. If crosslinking or polymerization of a modified prepolymer of these classes is desired, it should be conducted via alternative chemistry.

In one embodiment, the prepolymer modification reaction is carried out in a nonaqueous environment, in order to avoid simultaneous polymerization. This embodiment is especially preferred where greater degrees of modification are desired. It is, for example, most preferred where the modifying compound is a diamine or polyamine or contains a carboxyl group. It is also preferred where the prepolymer is monofunctional alcohol-based. Moreover, greater control can be exerted to modify particular percentages of the prepolymer by controlling the molar ratios.

Solvents such as those listed above for preparation of the prepolymer may be used. In addition, solvents such as toluene, 2-propanol, methanol, ethanol, pyridine, and other aprotic solvents may be used. The solvent should be dried prior to use, for example, by drying over molecular sieves. If methanol or ethanol are used, great care should be taken to thoroughly dry the solvent and to avoid storage prior to use. The isocyanate of the prepolymer may react with water present in the solvent rather than reacting with the modifying compound. To this extent, the prepolymer will undergo polymerization rather than derivatization.

In this embodiment (prepolymer modification in a dry, nonaqueous solvent), the prepolymer and the modifying compound are contacted in the solvent under ambient conditions. The concentration of prepolymer can vary greatly, from close to zero to almost 100%, but preferably between about 5.0 to about 50.0% (wt/wt) prepolymer is used. Although it is possible to derivatize the prepolymer in an ambient atmosphere, it will be preferred to conduct the reaction under a dry, inert atmosphere, such as dry nitrogen, in order to preserve the isocyanate groups. At ambient temperatures, the derivatization reaction typically will be complete in up to about one hour. However, it is preferred to allow a longer time for this step (i.e., about 4 to 24 hours) in order to ensure that the reaction has gone to completion.

In another embodiment, modification of the prepolymer takes place simultaneously with polymerization by contacting the prepolymer and modifying compound in the presence of water or another crosslinking agent. For example, an aqueous solution of the modifying compound may be used. The prepolymer becomes derivatized and also polymerized to some extent, due to the reaction of some of the isocyanate groups with the modifying compound and some with water. The degree of modification is controlled by the quantity of the modifying compound present in relation to the prepolymer, as well as the quantity of water present. Clearly, this embodiment is useful where partial modification is sought and where it is desired that the final product is a three-dimensional modified polymeric structure. This embodiment also is useful in those cases where the modifying compound is insoluble in non-aqueous solvents. The one-step modification reaction of this embodiment also may be advantageous in eliminating process operations.

The degrees of modification versus polymerization can be controlled by balancing the relative molar concentrations of modifying compound, prepolymer and water. That is, the prepolymer and the modifying compound are reacted in sufficient quantities to allow for reaction of the desired portion of the isocyanate groups of the prepolymer. These adjustments are within the skill of the art. Ambient conditions may be used for the modification reaction in this embodiment. The intended end use of the modified polymer will dictate the desired extent to which the isocyanate groups of the prepolymer are derivatized by reaction with the modifying compound. Anywhere up to 100% of the isocyanate groups may be modified according to this invention.

Modification of up to about 20% to 30% of the NCO groups will yield a modified prepolymer capable of significant polymerization. Under polymerizing conditions (that is, on exposure to water) a three-dimensional, highly crosslinked structure will be obtained which will be either a foam or gel, depending on the prepolymer selected. Such selection is well within the knowledge and ability of a person of ordinary skill in the art.

Conversely, all or most of the isocyanate groups of the prepolymer may be derivatized, yielding a modified prepolymer which is incapable of substantial polymerization or formation of a stable, three-dimensional structure. Where greater than about 50% (up to 100%) of the NCOs are modified, little or no polymerization will occur under polymerizing conditions. The composition essentially will remain in the form of modified prepolymer units. Where there is less than total (100%) modification, some crosslinking may occur on exposure to water, yielding small, isolated modified polymer units. The modified prepolymer and modified polymer units of this embodiment are soluble in aqueous solutions. As mentioned above, it may be possible to form a gel or polymer from these modified units, where the polymerization is through other chemistries. However, it should be clear that insufficient NCO-groups will remain for substantial polymerization through isocyanate chemistry. It is in this range (i.e., greater than about 50% modification) that diamine-, polyamine-, or carboxyl-modified prepolymers are prepared, as well as prepolymers based on monofunctional alcohols.

Modification in the middle range, that is, greater than about 20% to 30% and less than about 50% of the prepolymer isocyanate groups, also can be made according to this invention. Under polymerizing conditions, polymer strands or chains may form, increasing the viscosity of the modified preparation, although it is unlikely that a stable gel or foam will form. At this extent of modification, the modified polymer or prepolymer typically will be characterized by solubility in rather than reactivity with water, although at the lower end of the modification range some gelling or foaming will occur. In general, gelling or foaming will occur only where less than about one-third of the terminal NCO groups of the prepolymer are modified Polymerization As previously described, where up to about one-third of the isocyanate groups of the prepolymer are modified, polymerization may be accomplished by the addition of a stoichiometric excess of water or aqueous solution relative to the total remaining available isocyanate groups. Where the prepolymer has been modified to a greater extent, "polymerization" is somewhat of a misnomer, although the composition may be cured by final treatment of the modified prepolymer with water or an aqueous solution. In this case, the remaining isocyanate groups on the modified prepolymer are reacted with water to cure the modified composition, although little or no polymerization occurs due to the high percentage of NCO groups which have undergone reaction with the modifying compound. Any remaining NCO groups react with the water. Alternatively, the remaining NCO groups could be used to couple the modified prepolymer to a surface or to another compound.

The prepolymer solution may be shaped, poured or handled as necessary. Where extensive or precise shaping or handling is required, an aliphatic polyisocyanate should be used in preparing the prepolymer. As an alternative to shaping at this stage, the hydrated or foamed polymer may itself be cut to the desired size or shape.

A modified prepolymer-aqueous solution may be prepared, with or without an organic solvent, to initiate polymerization and curing. Once the solution is completely mixed, it should be left unagitated in order to allow crosslinking to occur. As polymerization begins to occur, gelling or foaming takes place, depending on whether a gel-forming or foam-forming prepolymer is used. At the gelling or foaming stage, the modified polymer sets and takes on the physical form of the final cured product, forming a semisolid elastic matrix. Setting time may be on the order of from about thirty seconds to about one hour. Unreacted isocyanate groups still will be present at this stage. A gel-forming polymer mixture loses its ability to flow, becoming a jelly-like solid or semi-solid mass. Where foam-forming prepolymers have been employed, the mixture foams and sets in a foamed configuration. Foaming is quite rapid. Alternatively, the modified prepolymer-organic solvent solution may be applied to the desired substrate and subsequently contacted with water or an aqueous solution to initiate polymerization and curing.

Preferably, water alone is used for polymerization and curing, but solutes or particulates may be present, if desired. Solutes which react with the isocyanate groups will become an integral part of the hydrogel. Care should be taken with such solutes since too high a concentration may result in excessive end-capping of the prepolymer to such an extent that polymerization will be precluded. It will generally be preferred to avoid using isocyanate-reactive compounds other than the modifying compound.

In preparing an aqueous solution containing the modified prepolymer, the modified prepolymer-to-water ratio should be about 1:1 to about 1:20, preferably about 1:5 to about 1:15. Setting time increases as the proportion of modified prepolymer in the aqueous solution decreases. The solution should be stirred or agitated until completely mixed and then allowed to stand so that a three-dimensional modified polymer structure may form.

Polymerization begins to occur spontaneously with formation of urea upon contact of the unmodified isocyanate groups with water. Catalysts or crosslinking agents are not required but are considered optional and may be used if desired. Suitable catalysts include organic tin salts (e.g., dibutyltin dilaurate) and tertiary amines. Suitable crosslinking agents include primary and secondary polyamines and polyfunctional isocyanates.

The polymer continues curing until the chemical reaction of all residual isocyanate groups with water is complete or approaches completion. Complete curing reaction may take hours, days or weeks, depending on the conditions and the polyisocyanate used, although it is essentially complete in about four to twenty-four hours. The curing time may be shortened by addition of chain terminating or inactivation agents, such as ethanolamine, which cause end-capping without chain extension. The final modified polymer product is a polyurea-urethane.

Where a hydrogel or foam is to be formed, only setting (that is, gelation or foaming) is required to set the shape of the modified polymer. However, complete or substantially complete curing is necessary in order to produce a biocompatible hydrated polymer which resists nonspecific protein binding. Complete isocyanate reaction may be ensured by soaking the polymer in water to reduce or eliminate the availability of residual isocyanate groups, or by incorporating chain terminating agents as described above. This eliminates residual isocyanate groups which may bind proteins which come into contact with the hydrated polymer.

Setting and curing time will vary, depending in part on the concentration of prepolymer present in the solution from which the polymer is formed. Setting time decreases with higher prepolymer concentrations. In addition, setting time depends on the type of polyisocyanate used in preparing the prepolymer. Aromatic polyisocyanate end-capped prepolymers will set rapidly, usually reacting in somewhat less than one minute, although the curing time may be longer. Prepolymers capped with aliphatic polyisocyanates have a longer setting time, typically about 20 to 90 minutes, and may take from up to several hours to several weeks for complete curing. If desired, the polymer may be subjected to a drying step.

When the modified polymer of this invention is prepared as a coating in the form of a thin film or a monomolecular or substantially monomolecular layer, a distinction between setting and curing is less apparent. In this embodiment, the modified prepolymer-organic solvent solution is deposited on a substrate and excess organic solvent is removed. Atmospheric moisture may be sufficient for polymerization of the gel coating or layer. Water is added to promote chain extension and crosslinking of the modified polymer on the substrate surface. This crosslinking is necessary to stabilize the coating, which otherwise would wash off under certain conditions, such as high water flow rates, or high or low pH, for example. The coating is subjected to this water treatment for about 15 minutes to about 24 hours, or longer, to ensure complete or substantially complete reaction of the isocyanate groups. If desired, the coating may be treated with a chain terminating agent, such as ethanolamine, to ensure reaction of the residual isocyanate groups.

Organic solvents may be useful in preparing hydrated polymers (i.e., hydrogels) according to this invention. During polymerization, the presence of a solvent enables the system to tolerate higher levels of excess isocyanate (over stoichiometric amounts) without causing disruption of the hydrated polymer formation. Carbon dioxide formed by the reaction of excess isocyanate monomer and water simply effervesces due to the system's low viscosity, rather than becoming entrapped to elicit foam formation. Of course, if foams are desired, polymerization would be conducted in the absence of or with much lower levels of solvent. The solvents listed above as being suitable for use in preparing the prepolymer may also be used here. In addition, methanol, ethanol, 2-propanol and dichloromethane, or mixtures thereof, may be used.

If an organic solvent is used in the preparation of the prepolymer, modified prepolymer or modified polymer, it most frequently will be removed prior to use of the polymer. If methanol is selected, it must be removed promptly (i.e., within a few minutes to several hours) in order to avoid excessive end-capping of the isocyanate groups, which will prevent polymerization. Solvent may be removed from the modified prepolymer prior to curing or may be allowed to evaporate during the process of depositing or coating the modified prepolymer onto a desired coatable substrate or forming the modified prepolymer into the desired shape. Alternatively, where a thin polymeric coating is desired, the modified prepolymer may be adsorbed onto a substrate directly from the solvent solution after which the entire coated substrate may be removed from the solvent. In most cases where curing is accomplished in the presence of the solvent, the solvent is removed from the modified polymer after curing, either by evaporation or by washing with water. In these cases, it is necessary to use a solvent which is water soluble. The organic solvent-modified prepolymer solution then will be compatible with the aqueous solution in which the polymer will be formed, resulting in an aqueous modified prepolymer solution, not an emulsion or dispersion.

Properties of the Modified Compounds

The properties of the modified prepolymers and polymers described herein are unique and offer significant advantages over conventional polymer systems. The modified prepolymer or polymer will be characterized by the specific reactivity provided by the second functional group of the modifying compound.

In one embodiment, the modified prepolymers of this invention have the ability to form three-dimensional foams or to gel large amounts of water. As discussed above, modification of up to about 30% of the prepolymer NCO groups will yield modified prepolymers with polymerization capacity. The general nature of the resulting foam or hydrogel will be based on the original prepolymer but will also be influenced by the modifying compound.

Modification of only a limited number of prepolymer isocyanate groups with polyfunctional compounds in this manner permits the introduction of functional or reactive groups while maintaining the ability of the prepolymer to undergo chain extension and polymerization by reacting with water or a crosslinking agent. A modified, but still biocompatible polymer can be formed which contains any of a wide variety of functional groups providing the novel specific reactivity characteristics of the modified polymer The specific properties of each modified polymer will depend, in this regard, on the reactive compound which is introduced to derivatize or modify the prepolymer. The second functional group of the modifying compound can be used for covalently binding another compound to the polymer, for specific activity of its own, for binding the polymer to a surface, or for other purposes.

An exception to the ability of the modified prepolymer to form water-insoluble gels or foams is the embodiment in which high percentages of the prepolymer units are modified, or end-capped, with the reactive compound. Insufficient reactive isocyanate groups are left for significant amounts of crosslinking to take place. The modified prepolymer of this embodiment is soluble in water and will readily form a solution. Some polymerization may occur, forming small modified polymer units. These units, of course, will have the reactivity characteristics provided by the second functional group of the modifying compound, and will be useful where that reactivity is desired.

The prepolymer's original resistance to nonspecific protein binding can be maintained during the modification reaction of this invention. If this is a desired characteristic, care should be taken to select a modifying compound which itself is not susceptible to nonspecific protein binding. For example, it would be desired to use uncharged hydrophilic modifying compounds, such as ethanolamine. Modifying compounds which are susceptible to nonspecific protein binding (for example, those having highly charged groups) should be avoided if non-specific protein binding would be problematic.

Where biocompatibility is desired, the modifying compound should be nontoxic. On the other hand, it may be desired to render the polymer toxic for certain purposes and modifying compounds can be selected with that in mind. For example, prepolymers might be modified with biocidal compounds or the like.

Use of aliphatic polyisocyanates in preparation of the prepolymers may further enhance the biocompatibility of the modified polymer product since the potential degradation products of aliphatic polyisocyanates are reported to be significantly less carcinogenic than those of aromatic isocyanates. However, if aromatic polyisocyanates are used, careful washing or other means for removing any unreacted isocyanate and related amine-containing by-products generally will be sufficient to render the modified polymer biocompatible.

Biocompatibility, as used herein to describe the hydrated polymers of this invention, refers to the resistance to adsorption of protein and to the lack of interactiveness with physiological surfaces, as discussed above. In addition, certain of the modified polymers of this invention have been demonstrated to be nontoxic to mammalian cells. However, this clearly depends on the selection of the modifying compound.

The examples which follow are given for illustrative purposes and are not meant to limit the invention described herein. The following abbreviations have been used throughout in describing the invention.
A—Angstrom(s)
° C—degrees Centigrade
cm—centimeter(s)
cps—centipoise(s)
DMEM—Dulbecco's Modified Eagle's Medium
DI—deionized
F12—F12 cell culture medium
gm—gram(s)
Hg—mercury
IDPI—isophorone diisocyanate
IU—International unit(s)
M—molar
$m^2$—square meter(s)
meq—milliequivalent(s)
mg—milligram(s)
min—minute(s)
ml—milliliter(s)
mm—millimeter(s)
mmoles—millimoles
$\mu$gm—microgram(s)
$\mu$m—micrometer(s)
MW—molecular weight
N—normal
NCO—isocyanate
ngm—nanogram(s)
PBS—phosphate buffered saline
ppm—parts per million
%—percent
TM—trademark
UV—ultraviolet
v—volume
wt—weight

EXAMPLE I (Preparation of Prepolymer A)

The polyol used to prepare the prepolymers of this invention, Pluracol V7 TM (BASF), a 7000 MW triol copolymer of ethylene oxide (75%) and propylene oxide (25%), was deionized and dried. Following this deionization procedure, 1687.46 gm Pluracol V7 was mixed with 165.0 gm isophorone diisocyanate (IDPI) and 0.93 gm Santonox R TM (Monsanto Chemical Co.) and heated at 70° C under dry nitrogen. Isocyanate levels were determined by addition of dibutylamine and back titration with standard acid. Fourteen days were required for the isocyanate concentration to reach 0.47 meq/gm (0.39 meq/gm=theoretical). The resulting prepolymer, designated Prepolymer A, was liquid at room temperature.

EXAMPLE II (Preparation of Prepolymer B)

A prepolymer was formed by mixing 300.0 gm deionized and dried TPEG10000 TM (Union Carbide Corp.) with 22.0 gm IPDI and 0.16 gm Santonox R. TPEG10000 is a 10,000 MW triol prepared from 100% homopolymeric ethylene oxide. The mixture was heated at 70° C under dry nitrogen as in Example I, until isocyanate values reached 0.36 meq/gm (theoretical=0.28 meq/gm). This prepolymer, designated Prepolymer B, formed a solid when cooled to room temperature.

EXAMPLE III (Preparation of Prepolymer C)

A prepolymer was formed by mixing 1570.0 gm deionized and dried BASF 1123 polyol (BASF) with 200.0 gm Desmodur W TM methylene bis(cyclohexyl diisocyanate) (Mobay Chemical Corp.). BASF 1123 polyol is a 6800 MW polyether triol comprised of 75% ethylene oxide and 25% propylene oxide. The mixture was heated to 85° C under dry nitrogen for a period of 2-3 days until an isocyanate level of 0.47 meq/gm was reached. The resulting prepolymer was liquid at room temperature and had a viscosity of 63,000 cps at 25° C. This prepolymer was designated Prepolymer C.

EXAMPLE IV (Preparation of Prepolymer D)

A prepolymer was prepared by dissolving 50.0 gm (0.0125 equiv. hydroxyl) of polyethylene glycol (8000 MW) (Sigma Chemical Co.) in 100 cc (78.2 gm) acetonitrile. To this was added 3.06 gm (0.0275 equiv. isocyanate) isophorone diisocyanate and 0.03 gm Santonox R. The solution was heated to 70° C under dry nitrogen in a dry, acid-washed glass flask for 14 days. The isocyanate level declined to 0.10 meq/gm at day 14 (theoretical=0.11 meq/gm). The prepolymer formed was designated Prepolymer D and was stored as a 25% solution in acetonitrile.

EXAMPLE V (Preparation of Prepolymer E)

A prepolymer was prepared by first dissolving 50.0 gm (0.0263 equiv. hydroxyl) polyethylene glycol monomethyl ether (MW 1900) (Polysciences, Inc.) in 100 ml (79.2 gm) acetonitrile. To this solution was added 6.43 gm (0.0578 equiv. isocyanate) isophorone diisocyanate and 0.03 gm Santonox R. The solution was heated under dry nitrogen at 70° C in an acid-washed glass flask for 8 days, at which time the isocyanate content was 0.15 meq/gm (theoretical=0.23 meq/gm). This prepolymer, designated Prepolymer E, was stored as a 42% solution in acetonitrile.

EXAMPLE VI (Preparation of Prepolymer F)

A prepolymer was prepared by mixing 848.8 gm of deionized and dried polyol BASF 1123 (BASF) with 91.6 gm isophorone diisocyanate in a one liter polyethylene bottle at room temperature with mechanical stirring for 30 minutes. Dry nitrogen was purged over the mix and the bottle was sealed with a screw cap and placed in an electric oven at 85° C. After 11 days the reaction was terminated. The product had an isocyanate value of 0.43 meq/gm and a viscosity of 62,000 cps at 25° C. This prepolymer was designated Prepolymer F (low temperature). A prepolymer was prepared in the identical manner except that it was incubated in an electric oven at 125° C. This prepolymer was designated Prepolymer F (high temperature).

EXAMPLE VII (Preparation of Prepolymer G)

Mono-methoxy poly(ethylene glycol) with a molecular weight of 550 (160 gm, 0.291 moles) was mixed with isophorone diisocyanate (69.0 gm, 0.310 moles) in a polyethylene bottle and purged with dry nitrogen. The sample was placed in an oven and the temperature maintained at 70° C for 20 hours. At that time, the sample was removed and the isocyanate level was determined to be 1.32 meq/gm. This product was labeled Prepolymer G.

EXAMPLE VIII (Preparation of Prepolymer H)

A polyether diol was obtained comprising 84% ethylene oxide and 16% propylene oxide, with a molecular weight of 2200 (Takeda). This diol (800 gm, 0.36 moles) was mixed with IPDI (163.4 gm, 0.74 moles) and placed in a polyethylene bottle under dry nitrogen. The sample was heated at 70° C for 10 days at which time the isocyanate level was found to be 0.75 meq/gm. The reaction was terminated at this point and the product was stirred under dry nitrogen. The product was labeled Prepolymer H.

EXAMPLE IX (Preparation of Prepolymer J)

A polyether triol was obtained comprising 82% ethylene oxide and 18% propylene oxide, with a molecular weight of 3600 (Asahi Glass). This triol (800 gm, 0.22 moles) was mixed with isophorone diisocyanate (149.1 gm, 0.67 moles) over dry nitrogen and placed in a polyethylene bottle. The sample was heated at 70° C for 12 days at which time the isocyanate level reached 0.72 meq/gm. The sample was labeled Prepolymer J and was stored under dry nitrogen at 4° C.

EXAMPLE X (3-Amino-1,2-Propanediol Derivative of Prepolymer A)

In this Example, 10.0 gm Prepolymer A (see Example I) (3.91 mmoles isocyanate) were dissolved in 20.0 ml dry 2-propanol. To this was added 3.56 ml (0.039 mmoles primary amine) of 1.0 mg/ml 3-amino-1,2-propanediol ("APD") in dry 2-propanol. The reaction was allowed to proceed overnight under ambient conditions. The solvent was then removed by flash evaporation. Under these conditions, it was expected that 1% of the isocyanate groups were covalently modified to contain a 1,2-dihydroxy substituent.

Verification was done by repeating the experiment, conducting the reaction in deutero-chloroform using sufficient APD to derivatize 100% of the isocyanate in order to provide an adequate signal, for subsequent analysis by carbon-13 NMR spectroscopy. It was found that the isocyanate carbon signal at ~121 ppm was eliminated, while a peak at ~160 ppm, corresponding to the urea carbonyl, was acquired. This change suggests reaction of the amine with the isocyanate to form a urea linkage.

EXAMPLE XI (Dibutylamine Modification of Prepolymer A)

Prepolymer A (Example I) (2.5 gm) (0.98 meq isocyanate) was dissolved in 50.0 ml methylene chloride. To this was added 1.25 ml of 0.1N dibutylamine (0.125 meq) in toluene. This calculates to be a modification of 12.8% of the NCO groups (i.e., a 7.8 excess of NCO groups over amino groups). This was allowed to react for one hour at ambient temperature under dry nitrogen. This partially dibutylamine-derivatized Prepolymer A was coated onto 5.0 gm silica (20–45 μm, 500 A pore diameter) by continuously filtering the solution over the silica bed until the solution evaporated. By thermal gravimetric analysis, it was determined that a coating weight of 16.7% was obtained. The coating was crosslinked with water.

Verification of prepolymer modification was done as in Example X, reacting 1.19 mmoles dibutylamine with 3.0 gm Prepolymer A (1.17 meq isocyanate) in deutero-chloroform. As before, the isocyanate peak was lost, while a urea carbonyl peak was obtained.

EXAMPLE XII (Albumin Modification of Prepolymer A)

A hydrogel was formed by mixing 0.12 gm Prepolymer A (Example I) with 0.60 ml of 0.02 mM sodium bicarbonate containing 0.6 mg bovine serum albumin (Sigma Chemical Co.). The mixture (pH 9.63) gelled in about 8.0 minutes under ambient conditions.

A second hydrogel was formed by mixing 0.10 gm Prepolymer A with 0.5 ml water containing 0.5 mg bovine serum albumin. The mixture (pH 6.95) gelled in about 27.0 minutes under ambient conditions.

A third hydrogel was formed by mixing 0.14 gm Prepolymer A with 0.7 ml phosphate buffered saline and 0.7 mg bovine serum albumin. The mixture gelled in about 37.0 minutes under ambient conditions.

EXAMPLE XIII (Fibronectin Modification of Prepolymer A)

A fibronectin-modified prepolymer was prepared by mixing 5.0 ml of 4.0 μgm/ml human plasma fibronectin ("hFN") in 0.1 M sodium bicarbonate buffer, pH 9.6, with 1.1 gm Prepolymer A. The mixture was allowed to form a gel at room temperature.

To confirm that the gel had been derivatized to contain bound hFN, 30.0 μl of the mixture was applied as a coat to 6.4 mm wells (30 μl per well) in a polystyrene assay plate prior to gelling. After coating the bottom surface of each well, excess polymer mixture was removed by aspiration and the coating allowed to gel at room temperature. The surfaces were thoroughly washed with phosphate buffered saline to remove any nonbound hFN or gel. The hFN was detected using a monoclonal antibody which specifically recognizes hFN in an ELISA assay protocol. In the absence of the anti-hFN antibody, the average absorbance per well was 0.001 absorbance units. Following treatment with the antibody, the absorbance per well was 0.423 absorbance units, demonstrating the presence of bound hFN in the derivatized polymer gel.

EXAMPLE XIV (Glucosamine Modification of Prepolymer A)

To prepare a glucosamine-modified hydrogel, 13.5 mg of D(+)glucosamine (Sigma Chemical Co.) was dissolved in 3.2 ml water (pH 7.0) and added to 1.57 gm Prepolymer A with mixing. The mixture was poured onto glass supports and allowed to gel at room temperature. Stable gels were formed.

These glucosamine-modified hydrogels served as substratum for the attachment and growth of LLC-PK1 porcine kidney cells in a mixture of Dulbecco's Modified Eagle's Medium and Ham's F-12 Nutrient medium (3:1) containing ten percent fetal bovine serum, and bovine aortic endothelial cells in M199 medium containing ten percent fetal bovine serum. Control hydrogels made from polymerization of Prepolymer A did not support the attachment and growth of these cells. No cell toxicity was observed with either derivatized or unmodified hydrogel.

EXAMPLE XV (Aminoethanesulfonic Acid Modification of Prepolymer A)

A solution was prepared by dissolving 126.0 mg aminoethanesulfonic acid (taurine) in 10.0 ml of 0.05 M phosphate buffer (pH 7.0). To 4.72 ml of the taurine solution was added 1.18 gm Prepolymer A, followed by thorough mixing. This ratio was equivalent to one mole of taurine amino group per mole of prepolymer NCO group. The soluble modified prepolymer was stirred overnight at room temperature and then dialyzed to remove excess taurine. The modified prepolymer dissolved in water, rather than exhibiting gel-forming properties. The modified prepolymer was characterized by size exclusion chromatography.

EXAMPLE XVI (Aminoethanesulfonic Acid Modification of Prepolymer F)

To 200.0 ml of a 1:1 solution of 2-propanol:phosphate buffer (0.05 M) (pH 7.0) was added 1.27 gm aminoethane-sulfonic acid (taurine). The mixture was stirred at room temperature until the taurine dissolved. With continued stirring, 5.0 gm Prepolymer F (low temperature) (dissolved in 5.0 ml 2-propanol) was added dropwise to the taurine solution. This calculates to be a 2-fold excess of taurine amino group over prepolymer NCO group. The dropwise addition continued for 15 minutes and the reaction was continued overnite at room temperature. The solvent was removed from the reaction mixture with a rotary evaporator under vacuum. The dried residue dissolved completely in 20.0 ml water.

EXAMPLE XVII (Ethanolamine Modification of Prepolymer F)

A solution was prepared by dissolving 500.0 mg ethanolamine in 100.0 ml water containing 0.1 ml of 1.0 M sodium bicarbonate, and adjusting the pH to 11.0. A 10.0 ml quantity of a solution of 19.67 gm Prepolymer F (low temperature) in 20.0 ml 2-propanol was added dropwise with stirring. This calculates to be a 5-fold excess of ethanolamine amino groups over prepolymer NCO groups. The modified compound was characterized by size exclusion chromatography.

EXAMPLE XVIII (Tyrosine Modification of Prepolymer F)

A solution was prepared by dissolving 1.63 gm L-tyrosine in 100.0 ml water containing 0.1 ml sodium bicarbonate and adjusting the pH to 11-12. A 5.0 gm quantity of Prepolymer F (low temperature) was dissolved in 10.0 ml 2-propanol and added to the tyrosine solution dropwise with stirring. This calculates to be a 5.5-fold excess of tyrosine amino groups over prepolymer NCO groups. The excess tyrosine was removed by dialysis against water.

The dialyzed composition was analyzed by gel filtration chromatography on Sephadex G-25. Tyrosine-modified prepolymer eluted in the excluded volume where the marker blue dextran eluted. Free tyrosine standard eluted at twice that elution volume. The dialyzed composition appeared to be free of free tyrosine by this analysis.

EXAMPLE XIX (Aminoethylphosphonic Acid Modification of Prepolymer F)

A solution was prepared by dissolving 0.5 gm 2-aminoethylphosphonic acid in 50.0 ml of 0.01 N sodium bicarbonate/0.5 N sodium hydroxide (pH 10–11). A solution of 2.5 gm Prepolymer F (low temperature) in 5.0 ml 2- propanol was added with stirring at room temperature. This calculates to be a 4.8-fold excess of amino groups over NCO groups. Stirring was contained for two hours. The composition was dialyzed against water to remove excess aminoethylphosphonic acid.

EXAMPLE XX (Cystamine Modification of Prepolymer F)

A solution was prepared by dissolving 37.1 mg cystamine dihydrochloride in 15.0 ml of 50.0 mM sodium borate (pH 8.5). This solution was added to 1.0 gm Prepolymer F (low temperature) and stirred until the Prepolymer F appeared to be dissolved. Formation of gel occurred at room temperature in approximately 12 hours. Excess cystamine was washed away by adding 20.0 ml PBS to the gel and incubating at 31° C for one hour. The PBS was poured off and the washing procedure was repeated twice.

To the gel, 5.0 ml of 200.0 mM mercaptoethanol solution in P(S was added to reduce the cystamine disulfide bond in order to activate the second functional group of the modifying compound. After 24 hours the gel had partially dissolved and an additional 2.0 ml of 0.1 M mercaptoethancl solution was mixed with 2.0 ml of the gel/solution, to fully dissolve the gel. The solution was then filter sterilized.

EXAMPLE XXI (Cystamine Modification of Prepolymer A)

A solution was prepared by dissolving 74.2 mg cystamine dihydrochloride in 30.0 ml of 50.0 mM sodium bicarbonate (pH 8.5). This calculates to be a 1.06-fold excess of prepolymer NCO groups over cystamine amino groups, for modification of approximately all of the prepolymer NCO groups. Two grams of Prepolymer A were dissolved in the solution, which was then poured into a glass plate to produce a thin layer which gelled-in approximately 12 hours.

To reduce the cystamine disulfide bonds and dissolve the gel, 30.0 ml of 55 mM mercaptoethanol was added. The product was then filter sterilized.

EXAMPLE XXII (Cystamine Modification of Prepolymer B)

A solution was prepared by dissolving 1.3 gm cystamine dihydrochloride in 150.0 ml of 50.0 mM sodium bicarbonate (pH 8.5). To this solution, 10.0 gm Prepolymer B (as a 50% (wt/wt) solution in acetonitrile) was added by stirring. After four hours with stirring, mercaptoethanol was added to reduce the cystamine disulfide bond. Excess cystamine and mercaptoethanol were removed by dialysis against distilled water.

EXAMPLE XXIII (Cysteamine Modification of Prepolymer F)

A solution was prepared containing 40.0 mM cystamine dihydrochloride and 55.0 mM 2-mercaptoethanol in 25.0 ml PBS, thereby reducing the internal disulfide bond of cystamine. Tc the solution, 0.5 gm Prepolymer F (low temperature) was added dropwise with stirring. The solution was stirred overnite at room temperature. Excess cysteamine was removed by dialysis against water. In this Example, the prepolymer modification was via the thiolate group of cysteamine, leaving the amino group as the second functional group. The result was confirmed by NMR analysis.

EXAMPLE XXIV (Cystamine Modification of Prepolymer G)

Prepolymer G (2.48 gm, 3.2 meq NCO) was dissolved in 2.5 ml 2-propanol. Cystamine dihydrochloride (7.32 gm, 32.5 mmoles) was dissolved in 50.0 ml 0.05M sodium phosphate (pH 7.0), and the pH was readjusted to 7.0 with 1N NaOH. The prepolymer solution was added to the cystamine solution dropwise with stirring over a 10 minute period. Stirring at room temperature was continued for 24 hours at which time the product was dialyzed against distilled water for 24 hours to remove low molecular weight material, including unreacted cystamine.

EXAMPLE XXV (Cystamine Modification of Prepolymer H)

Prepolymer H (2.50 gm, 1.88 meq NCO) was dissolved in 2.5 ml 2-propanol. Cystamine dihydrochloride (4.22 gm, 18.7 mmoles) was dissolved in 50.0 ml 0.05 M sodium phosphate (pH 7.0), and the pH was readjusted to 7.0 with 1N NaOH. The prepolymer solution was added dropwise with stirring to the cystamine solution. After stirring for 24 hours at room temperature the product was dialyzed against distilled water for 24 hours to remove low molecular weight material, including unreacted cystamine.

EXAMPLE XXVI (Cystamine Modification of Prepolymer J)

Prepolymer J (2.48 gm, 1.79 meq NCO) was dissolved in 2.5 ml 2-propanol. Cystamine dihydrochloride (4.02 gm, 17.9 mmoles) was dissolved in 50.0 ml 0.05 M sodium phosphate (pH 7.0), and the pH was readjusted to 7.0 with 1N NaOH. The prepolymer solution was added dropwise with stirring to the cystamine solution and stirring was continued at room temperature for 24 hours. The product was then dialyzed against distilled water for 24 hours to remove low molecular weight materials, including unreacted cystamine.

EXAMPLE XXVII (Cystamine Modification of HYPOL TM Hydrogel)

HYPOL Hydro9el polyurethane prepolymer (2.52 gm, 2.02 meq NCO) (Grace Specialty Chemicals Co., W.R. Grace & Co.-Conn.), was dissolved in 2.5 ml 2-propanol. Cystamine dihydrochloride (4.54 gm, 20.2 mmoles) was dissolved in 50.0 ml 0.05M sodium phosphate (pH 7.0), and the pH was readjusted to 7.0 with 1N NaOH. The prepolymer solution was added to the cystamine solution dropwise with stirring. Stirring was continued for 24 hours at room temperature at which time the product was dialyzed for 24 hours against distilled water to remove low molecular weight materials, including unreacted cystamine.

EXAMPLE XXVIII (Cystamine Modification of HYPOL TM X6100)

HYPOL X6100, an experimental hydrophilic urethane prepolymer (50.0 gm, 93 meq NCO) (Grace Specialty Chemicals Co., W.R. Grace & Co.-Conn.), was added to a solution of cystamine dihydrochloride (10.5 gm, 46.4 mmoles) in 50.0 mM sodium bicarbonate (pH 7.0). The solution was stirred overnight at room temperature.

EXAMPLE XXIX (Peptide Modification of Prepolymer F)

A pentapeptide with a sequence of tyrosine-arginine-glycine-aspartate-serine (single letter code YRGDS) was obtained from Bachem, Inc. The peptide was 98% pure and had a molecular weight of 596.7. A solution of YRGDS was prepared in 0.05M sodium phosphate (pH 7.0), at a concentration of 5.0 mg/ml. To 0.3 ml of the peptide solution was added 30.0 μl of a 200.0 mg/ml solution of Prepolymer F (high temperature) in 2-propanol. These volumes provide a slight excess of peptide (2.51 micromoles) over prepolymer isocyanate (2.4 microequivalents). The mixture was kept at room temperature for 2.5 hours at which time it was analyzed by gel permeation HPLC. The separation system consisted of a Zorbax TM GF250 column (E.I. DuPont de Nemours Co.) and a mobile phase of 0.05M sodium phosphate, 0.3M NaCl (pH 7.0) at a flow rate of 0.5 ml/min. With these conditions, the void and internal volumes were 14.0 minutes (Blue Dextran) and 24.0 minutes (sodium azide), respectively. Peptide-prepolymer conjugate was identified as a broad peak eluting in the 14–20 minute time period. This was clearly separated from unreacted peptide, which eluted at 24 minutes. Free peptide was separated from the bound form using a disposable PD-10 column (Pharmacia).

EXAMPLE XXX (Tyramine Modification of Prepolymer F)

Prepolymer F (low temperature) (5.09 gm, 2.19 meq NCO) was dissolved in 5.0 ml 2-propanol. This solution was added dropwise with stirring to 50.0 ml of 0.05M sodium phosphate (pH 7.0) containing 0.38 gm (2.19 mmoles) tyramine hydrochloride (Sigma Chemical Co.). The resulting turbid solution was stirred for 17 hours at room temperature. A 10.0 ml portion of the product was dialyzed against 500.0 ml water for 46 hours with 4 changes to remove unreacted free tyramine.

EXAMPLE XXXI (2,2'-Dithiodiethanoic Acid Modification of Prepolymer F)

A solution was prepared by dissolving 170.0 mg 2,2'-dithiodiethanoic acid in 20.0 ml acetonitrile. This solution was added to 4.4 gm Prepolymer F (high temperature) and stirred until the prepolymer appeared to be dissolved. This calculates to be 1.0 mole equivalence of carboxylic groups to prepolymer NCO groups. Carbon-13 NMR spectrum of the sample after one week showed that only 5–10% of the NCO groups had reacted with the carboxylic group. At that point an equivalent amount of N-methyl imidazole was added to ionize all the carboxylic groups. Gel formation occurred at room temperature in approximately 24 hours. The gel was shaken for 4 hours with 20.0 ml of acetonitrile and excess 2,2'-dithiodiethanoic acid and N-methyl imidazole was poured off.

To the washed gel, 20.0 ml of 200 mM 2-mercaptoethanol solution in acetonitrile was added to reduce the disulfide bond of 2,2'-dithiodiethanoic acid in order to activate the second functional group of the modifying compound. After 12 hours, the gel had completely dissolved.

EXAMPLE XXXII (Gel Formation from Modified Prepolymers)

Modified prepolymers were formed by adding each modifying compound listed in Table I to Prepolymer A in sufficient quantities to modify 10%, 20% or 50% of the prepolymer NCO groups. The procedures were as follows:

A stock solution was made by dissolving 107.5 mg of D(+)glucosamire in 10.0 ml of 0.05 M sodium phosphate (pH 7.0, phosphate buffer). Dilutions of this stock were used to make up the derivatizing solution. A 50% modified prepolymer was prepared by mixing 4.0 ml glucosamine stock solution with 1.0 gram of Prepolymer A. A 20% modified prepolymer was prepared by mixing 1.6 ml glucosamine stock diluted to 4.0 ml with phosphate buffer with 1.0 gm Prepolymer A. A 10% modified prepolymer was prepared by mixing 0.8 ml of stock glucosamine diluted to 4.0 ml with phosphate buffer with 1.0 gm Prepolymer A. In each case, the Prepolymer A was dissolved in 1.0 ml acetonitrile solvent before being mixed with the glucosamine. After thorough mixing, each derivative was allowed to stand overnight at room temperature. Each mixture was visually inspected for gel formation. Stable gels did not dissolve when washed with ten volumes of water.

This procedure was repeated for each of the modifying compounds listed in Table I, to prepare the 10%, 20% and 50% derivatives. The results are shown in Table I.

TABLE I

| Modifying Compound | Stable Gel Formation | | |
|---|---|---|---|
| | 10% | 20% | 50% |
| Control (Prepolymer A) | Yes | Yes | Yes |
| Glucosamine | Yes | No | No |
| 3-Amino-1,2-propanediol | Yes | Yes | No |
| 3-Amino-1-propane sulfonic acid | Yes | Yes | No |
| 3-Aminophenylboronic acid | Yes | Yes | No |
| 2-Amino-2-deoxy-D-galactose (galactosamine) | Yes | No | No |
| 2-Aminoethane sulfonic acid (taurine) | Yes | Yes | No |
| 2-Aminoethanol (ethanolamine) | Yes | Yes | No |
| 1-Amino-1-deoxy-D-galactose | Yes | Yes | No |
| p-Aminophenyl-1-thio-beta-D-galactose | Yes | Yes | No |
| p-Aminophenyl-alpha-D-glucose | Yes | Yes | No |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A modified hydrophilic prepolymer derived from prepolymer units which are oxyethylene-based alcohols having essentially all of the hydroxyl groups capped with polyisocyanate, wherein said prepolymer units have been modified by reaction with either
   (1) a modifying compound having a first functional group which is (i) a sulfhydryl group under conditions which form a thiolate anion (ii) a hydroxyl group, or (iii) an amino group contained in a monoamine compound, and having a second functional group which is substantially less isocyanate-reactive than said first functional group, such that at least a portion of the isocyanate groups of said prepolymer are modified, or (2) a modifying compound having a first functional group which is a carboxyl group or an amino group contained in a diamine or polyamine compound, and a second functional group which is substantially less isocyanate-reactive than said first functional group, such that substantially all of the isocyanate groups of said prepolymer are modified.

2. The modified prepolymer of claim 1 in which said first functional group is a sulfhydryl group under conditions which form the thiolate anion.

3. The modified prepolymer of claim 2 in which said modifying compound is treated with a base catalyst or a reducing agent to form said thiolate ion.

4. The modified prepolymer of claim 3 in which said base catalyst is a tertiary amine.

5. The modified prepolymer of claim 3 in which said reducing agent is sodium borohydride.

6. The modified prepolymer of claim 1 in which said diols or polyols are capped with an aliphatic or cycloaliphatic polyisocyanate.

7. The modified prepolymer of claim 6 in which said polyisocyanate is isophorone diisocyanate or methylene bis (cyclohexyl diisocyanate).

8. The modified prepolymer of claim 1 in which said modifying compound has a first functional group which is a sulfhydryl group or a hydroxyl group and said prepolymer is modified by reaction with sufficient quantities of said modifying compound to modify up to about 20 to about 30% of the isocyanate groups of said prepolymer.

9. The modified prepolymer of claim 1 in which said modifying compound has a first functional group which is a sulfhydryl group or a hydroxyl group and said prepolymer is modified by reaction with sufficient quantities of said modifying compound to modify up to 100% of the isocyanate groups of said prepolymer.

10. The modified prepolymer of claim 1 in which said modifying compound has a first functional group which is a sulfhydryl group, said modified prepolymer containing one or more thiourethane linkages.

11. The modified prepolymer of claim 1 in which said modifying compound has a first functional group which is a hydroxyl group, said modified prepolymer containing one or more urethane linkages.

12. The modified prepolymer of claim 1 in which said modifying compound has a first functional group which is a carboxyl group, said modified prepolymer containing one or more anhydride or amide linkages.

13. The modified prepolymer of claim 1 in which said modifying compound has a first functional group which is an amino group, said modified prepolymer containing one or more urea linkages.

14. The modified prepolymer of claim 1 in which said modifying compound has a first functional group which is a carboxyl group or which is an amino group contained in a diamine or polyamine compound and said modifying compound is present in molar excess of at least 2:1 over the isocyanate groups of said prepolymer.

15. A modified hydrophilic polymer derived from the modified prepolymer of claim 1.

16. The modified polymer of claim 15 which is a three-dimensional hydrogel or a foam structure.

17. The modified polymer of claim 15 which is a small, water soluble polymeric unit.

18. The modified polymer of claim 15 which is biocompatible.

19. The modified polymer of claim 15 which is characterized by a surface which is generally resistant to nonspecific protein adsorption but which is modified to contain free functional groups which exhibit specific reactivity, said free functional groups corresponding to the second functional group of the modifying compound.

20. A modified crosslinked hydrophilic polyurea-urethane polymer prepared by reacting together water and a modified prepolymer in a prepolymer-to-water ratio of about 1:1 to about 1:20, said modified prepolymer prepared by:

(a) reacting diols or polyols with polyisocyanate at an isocyanate-to-hydroxyl ratio of about 1.8 to about 2.2 so that essentially all of the hydroxyl groups of said diols or polyols are capped with polyisocyanate, resulting in an isocyanate-endcapped prepolymer, and (b) reacting said prepolymer with a modifying compound having a first functional group which is (i) a sulfhydryl group under conditions which form a thiolate anion (ii) a hydroxyl group, or (iii) an amino group contained in a monoamine compound, and having a second functional group which is substantially less isocyanate-reactive than said first functional group, said modifying compound present in quantities sufficient to modify up to about 20 to about 30% of the isocyanate groups of said prepolymer.

21. The modified polymer of claim 20 in which said prepolymer and said reactive compound are reacted in a nonaqueous solvent.

22. The modified polymer of claim 20 in which said prepolymer and said modifying compound are reacted in the presence of water, resulting in simultaneous modification of said prepolymer and polymerization of the modified prepolymer.

23. The modified polymer of claim 20 in which said first functional group is a sulfhydryl group, wherein said modified polymer comprises thiourethane and urea-urethane linkages.

24. The modified polymer of claim 20 in which said first functional group is a hydroxyl group, wherein said modified polymer comprises urethane and urea-urethane linkages.

25. The modified polymer of claim 20 in which said first functional group is an amino group, wherein said modified polymer comprises urea and urea-urethane linkages.

26. A method for modifying a hydrophilic prepolymer, the units of which are oxyethylene-based alcohols having essentially all of the hydroxyl groups capped with polyisocyanate, in order to insert into said prepolymer free functional groups which exhibit specific reactivity, comprising:

(a) adding siad prepolymer to a solution of a modifying compound having a first functional group which is a sulfhydryl group under conditions which form a thiolate anion, (ii) a hydroxyl group, (iii) a carboxyl group or (iv) an amino group and a second functional group which is at least substantially isocyanate-non-reactive, and (b) allowing reaction between the isocyanate groups of said prepolymer and the first functional groups of said modifying compound to yield modified prepolymer.

27. The method of claim 26 in which a large molar excess of said modifying compound is used.

28. The method of claim 26 in which substantially all of the isocyanate groups of said prepolymer are modified.

29. The method of claim 26 in which the reaction is conducted in a nonaqueous environment.

30. The method of claim 26 in which the prepolymer units are ethylene-based diols or polyols, the modification reaction is conducted in an aqueous environment and said prepolymer is simultaneously modified and polymerized.

31. The modified prepolymer of claim 1 in which said diols or polyols are capped with an aromatic polyisocyanate.

32. The modified prepolymer of claim 31 in which said aromatic polyisocyanate is toluene diisocyanate.

* * * * *

UNITED STATES PATENT AND TRADEMARK OFFICE
CERTIFICATE OF CORRECTION

PATENT NO. : 4,940,737
DATED : July 10, 1990
INVENTOR(S) : Braatz et al.

It is certified that error appears in the above-identified patent and that said Letters Patent is hereby corrected as shown below:

Claim 8, line 3, after "is" delete "a" and insert — said —.

Claim 9, line 3, after "is" delete "a" and insert — said —.

Claim 10, line 3, after "is" delete "a" and insert — said — and after "sulfhydryl group" insert — and a second functional group which is an amino or carboxyl group —.

Claim 11, line 3, after "hydroxyl group", insert — and a second functional group which is a carboxyl or sulfhydryl —.

Claim 12, line 3, after "carboxyl group", insert — and a second functional group which is a sulfhydryl group —.

Claim 13, line 3, after "amino group", insert — and a second functional group which is a member of the group consisting of hydroxyl, carboxyl, sulfonic acid, sulfhydryl, phosphonic acid and boronic acid groups —.

line 4, after "linkages", insert — and wherein said modified prepolymer is biocompatible.

UNITED STATES PATENT AND TRADEMARK OFFICE
CERTIFICATE OF CORRECTION

PATENT NO.   :   4,940,737

DATED        :   July 10, 1990

INVENTOR(S)  :   Braatz et al.

It is certified that error appears in the above-identified patent and that said Letters Patent is hereby corrected as shown below:

Claim 23, line 2,   after "is" delete "a" and insert -- said -- and after "sulfhydryl group" insert -- and said second functional group is an amino or carboxyl group --.

Claim 24, line 2,   after "hydroxyl group", insert -- and said second functional group is a carboxyl or sulfhydryl group --.

Claim 25, line 2,   after "amino group", insert -- and said second functional group is a member of the group consisting of hydroxyl, carboxyl, sulfonic acid, sulfhydryl, phosphonic acid and boronic acid groups --.

line 4,   after "linkages", insert -- and wherein said modified prepolymer is biocompatible --.

Signed and Sealed this

Twenty-first Day of April, 1992

Attest:

HARRY F. MANBECK, JR.

Attesting Officer        Commissioner of Patents and Trademarks